US005620428A

United States Patent [19]
Hand

[11] Patent Number: 5,620,428
[45] Date of Patent: Apr. 15, 1997

[54] SUCTION CANISTER APPARATUS AND METHOD

[75] Inventor: Joseph M. Hand, Sheboygan Falls, Wis.

[73] Assignee: Bemis Manufacturing Company, Sheboygan Falls, Wis.

[21] Appl. No.: 365,695

[22] Filed: Dec. 29, 1994

[51] Int. Cl.[6] .................................................... A61M 1/00
[52] U.S. Cl. ........................ 604/317; 604/319; 220/601; 220/23.86; 220/23.6
[58] Field of Search ..................... 604/317, 319, 604/322, 326, 415, 416; 220/23.6, 23.83, 571, 601, 2, 23.86, 367.1, 272.5; 206/509; 215/309

[56] References Cited

U.S. PATENT DOCUMENTS

| | | | |
|---|---|---|---|
| 3,699,964 | 10/1972 | Ericson . | |
| 3,866,608 | 2/1975 | Reynolds et al. | 604/319 |
| 4,015,603 | 4/1977 | Kurtz et al. . | |
| 4,112,948 | 9/1978 | Kurtz et al. . | |
| 4,258,824 | 3/1981 | Kurtz et al. | 181/233 |
| 4,306,557 | 12/1981 | North | 604/319 |
| 4,384,580 | 5/1983 | Leviton | 604/119 |
| 4,484,920 | 11/1984 | Kaufman et al. | 604/416 |
| 4,629,159 | 12/1986 | Wellenstam | 251/149.6 |
| 4,704,106 | 11/1987 | Shave et al. | 604/319 |
| 4,715,855 | 12/1987 | D'Antonio et al. | 604/320 |
| 4,785,963 | 11/1988 | Magley | 220/266 |
| 4,795,448 | 1/1989 | Stacey et al. | 604/319 |
| 4,809,860 | 3/1989 | Allen | 604/319 |
| 4,870,975 | 10/1989 | Cronk et al. | 604/319 |
| 4,889,531 | 12/1989 | D'Antonio et al. | 604/319 |
| 4,902,284 | 2/1990 | D'Antonio et al. | 604/320 |
| 4,926,915 | 5/1990 | Deussen et al. | 141/290 |
| 4,955,874 | 9/1990 | Farrar et al. | 604/319 |
| 5,011,470 | 4/1991 | Kurtz et al. | 604/4 |
| 5,026,358 | 6/1991 | Everett, Jr. et al. | 604/320 |
| 5,027,872 | 7/1991 | Taylor et al. | 141/347 |
| 5,121,778 | 6/1992 | Baker et al. | 141/319 |
| 5,195,994 | 3/1993 | Dieringer | 604/283 |
| 5,242,434 | 9/1993 | Terry | 604/317 |
| 5,273,083 | 12/1993 | Burrows | 141/18 |
| 5,300,050 | 4/1994 | Everett, Jr. et al. | 604/320 |
| 5,437,836 | 8/1995 | Yamada | 604/317 |
| 5,470,324 | 11/1995 | Cook et al. | 604/319 |

Primary Examiner—John G. Weiss
Assistant Examiner—Mark O. Polutta
Attorney, Agent, or Firm—Michael, Best & Friedrich

[57] ABSTRACT

A suction canister including a patient port, a vacuum port, a chamber, and a protrusion including a thin portion which defines a passageway, the passageway extending into the chamber such that the protrusion can be broken to provide communication between the passageway and the chamber to enable draining of fluid from the suction canister.

42 Claims, 2 Drawing Sheets

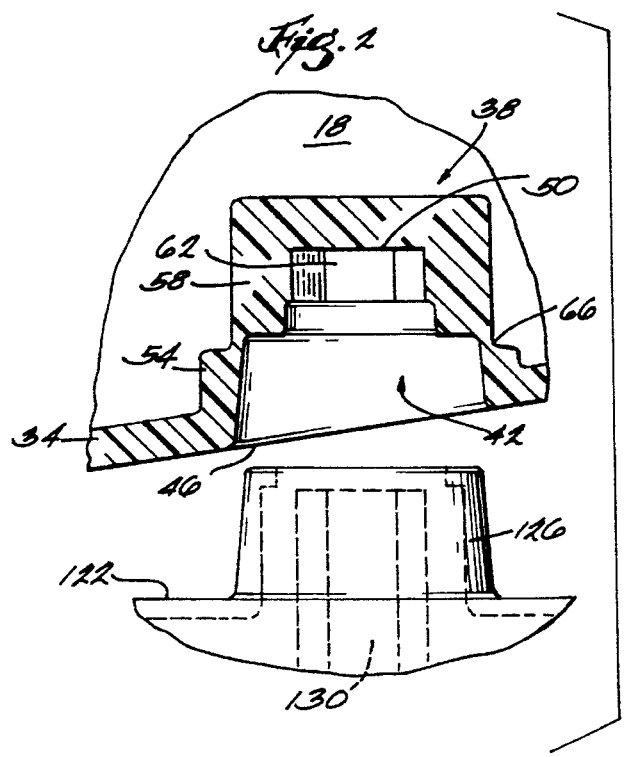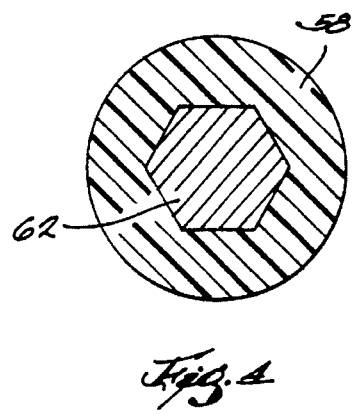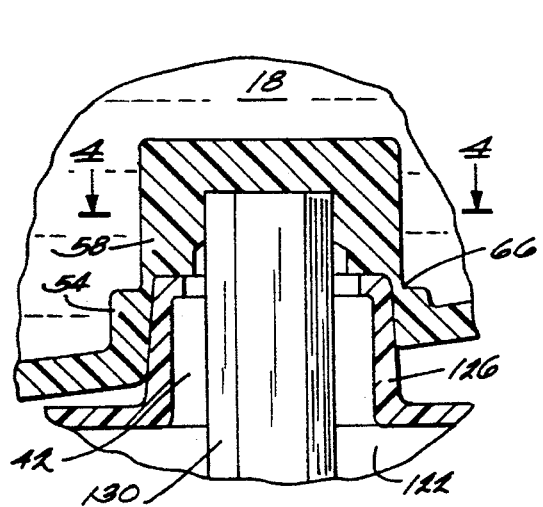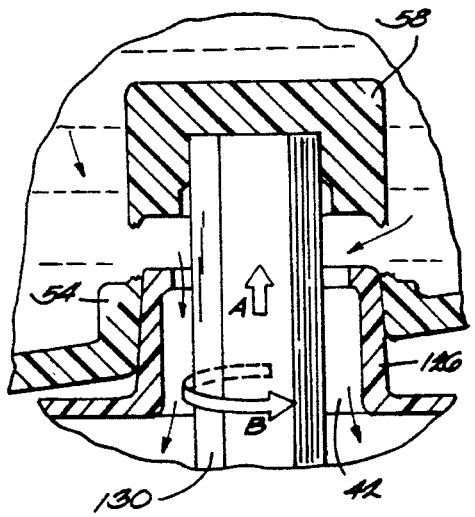

SUCTION CANISTER APPARATUS AND METHOD

FIELD OF THE INVENTION

The invention relates to a suction canister used in the collection of fluids such as from a patient during a surgical procedure and a method for doing the same.

BACKGROUND OF THE INVENTION

Suction canisters are used in hospital environments and particularly during various surgical procedures to store drained bodily fluid from a patient. In general, suction canisters are used in conjunction with a vacuum source which enables bodily fluid to be drained from the patient and stored in the canister. Each canister generally includes a receptacle for holding the bodily fluid, a lid with a vacuum port and a patient port, a suction conduit connecting the vacuum port to a vacuum source, and a patient conduit for conveying the bodily fluid from the patient into the receptacle through the patient port. When the suction conduit is connected to the vacuum source, a negative pressure gradient is created in the interior of the receptacle so that the bodily fluid is drawn from the patient and into the suction canister via the patient conduit.

It has become important in environments such as hospitals to eliminate the handling of and thus reduce employee exposure to bodily fluids. Currently, hospitals dispose of such bodily fluid in various ways. Bodily fluid can be poured from the suction canister down the hospital sink and into the sewer system, can be incinerated as a liquid or solid, or can be disposed of at an approved hazardous waste site. If hospital employees have to handle the bodily fluid, spattering of the bodily fluid can result in hospital employees contacting the hazardous fluid.

SUMMARY OF THE INVENTION

The invention provides a suction canister including a container having a chamber for collecting fluids, a patient port, and a vacuum port. The patient and vacuum ports communicate with the chamber. When a vacuum is created in the chamber via the vacuum port, fluid is thereby drawn into the container via the patient port. The chamber is partially defined by a wall, preferably the bottom wall, including a protrusion extending into the chamber. The protrusion defines a passageway having an open outer end and a closed inner end. The protrusion includes a thin portion such that the protrusion can be broken to provide communication between the passageway and the chamber for draining fluid contained in the suction canister.

The invention also provides a method of removing body fluids from a patient and disposing of the body fluids. The method includes the steps of providing a molded suction canister including a molded-in drain, providing a drainage device for automatically opening the molded-in drain and draining the contents of the suction canister, collecting body fluids in the suction canister, connecting the suction canister to the drainage device, and operating the drainage device so that the drainage device opens the drain and drains the contents of the suction canister.

The invention provides a suction canister that is easily drained of potentially hazardous fluid without contact with the fluid. The suction canister when used in conjunction with a drainage device allows a convenient means of disposing of the fluid content.

Other features and advantages of the invention will become apparent to those of ordinary skill in the art upon review of the following drawings, description and claims.

BRIEF DESCRIPTION OF THE DRAWINGS

FIG. 2 is a partial sectional view of the suction canister and the drainage device;

FIG. 3 is a view similar to FIG. 2 with the suction canister connected to the drainage device;

FIG. 4 is a view taken along line 4—4 of FIG. 3; and

FIG. 5 is a view similar to FIG. 3 with the tool of the drainage device breaking the protrusion of the suction canister.

Figure 1:
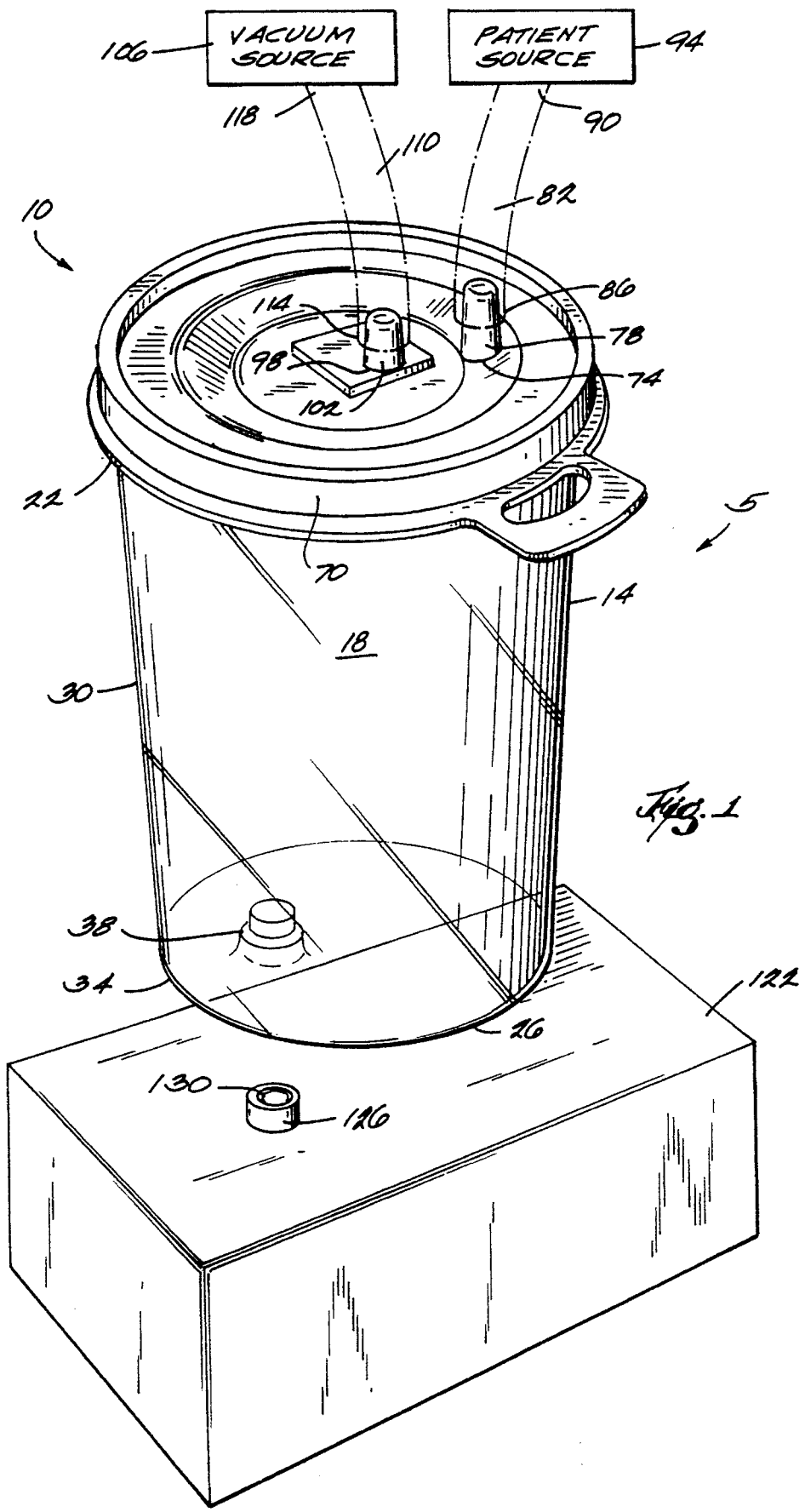
FIG. 1 is perspective view of an apparatus embodying the invention.

Before one embodiment of the invention is explained in detail, it is to be understood that the invention is not limited in its application to the details of construction and the arrangement of components set forth in the following description or illustrated in the drawings. The invention is capable of other embodiments and of being practiced or being carried out in various ways. Also, it is to be understood that the phraseology and terminology used herein is for the purpose of description and should not be regarded as limiting.

DETAILED DESCRIPTION OF THE PREFERRED EMBODIMENT

Referring now to the drawings in which like reference numerals refer to like parts throughout the views, there is shown in FIG. 1 an apparatus 5 embodying the invention. The apparatus comprises a suction canister 10. The suction canister includes a container 14 which defines a chamber 18 for collecting drained fluid. The container 14 is preferably plastic and is injection molded. The container 18 has an open upper end 22 and a closed lower end 26. The container 18 is defined by an annular side wall 30 and by a bottom wall 34. The bottom wall 34 includes a molded-in drain formed by a protrusion 38 extending into the chamber 18. By "molded-in" it is meant that the container 14 and the drain are formed in a single injection molding process.

As best shown in FIG. 2, the protrusion 38 defines a passageway 42 that tapers upwardly and has an open lower or outer end 46 and a blind or closed upper or inner end 50. More particularly, the protrusion 38 includes a first wall portion 54. The first wall portion 54 defines the outer end 46 of the passageway 42. As shown in FIG. 2, the first wall portion 54 is not uniform in height throughout its entire circumference due to a curvature of the bottom wall 34. However, it should be noted that the first wall portion 54 can be uniform in height throughout its circumference. Further, the height of the first wall portion 54 is preferably minimized to minimize the volume of fluid that remains in the suction canister 10 after it has been drained.

The protrusion 38 also includes a second wall portion 58 that defines the closed inner end 50 of the passageway 42. The second wall portion 58 defines an outwardly or downwardly opening, non-circular socket 62 at the inner end 50 of the passageway 42 as best shown in FIGS. 2 and 4. The socket is preferably hexagonal.

Referring now to FIG. 2, a thin or frangible wall portion 66 integrally connects the first wall portion 54 and the second wall portion 58. As will be explained in more detail hereafter, the frangible wall portion 66 can be broken to provide communication between the passageway 42 and the chamber 18 to enable draining of the fluid from the suction canister 10. The frangible wall portion 66 is small in size to provide for ease of breakage when draining is desired yet is also strong enough to withstand the tensile and circumferential stresses when a vacuum is created in the chamber 18 when the suction canister 10 is being filled with fluid. Further, due to the placement and configuration of the frangible wall portion 66 and the socket 62, inadvertent breaking of the protrusion 38 is minimized.

As shown in FIG. 1, the suction canister 10 also includes a lid 70 which closes the upper end 22 of the container 14. The lid 70 has therein a patient port 74 which communicates with the chamber 18. Extending upwardly from the patient port is a patient port wall 78. To enable communication between the fluid to be drained and the patient port 74, a patient conduit 82 is affixed to the patient port wall 78 by forcing one end 86 of the patient conduit 82 over the patient port wall 78. The other end 90 of the patient conduit 82 communicates with the fluid to be drained such as in a patient cavity 94. When the patient conduit 82 is not attached to the patient port wall 78, a cap (not shown) can be placed over the patient port wall 78 to prevent any fluid from leaking from the suction canister 10.

The lid 70 of the suction canister 10 also includes a vacuum port 98 which communicates with the chamber 18 via a filter (not shown). The filter can be, for example, a hydrophobic filter. Extending upwardly from the vacuum port 98 is a vacuum port wall 102. To enable a vacuum to be created in the chamber 18 of the suction canister 10, the vacuum port 98 communicates with a vacuum source 106 via a suction conduit 110. The suction conduit 110 is affixed to the vacuum port wall 102 by forcing one end 114 of the suction conduit 110 over the vacuum port wall 102. The other end 118 of the suction conduit 110 is placed in communication with the vacuum source 106. The filter prevents contamination of the vacuum source 106. When the suction conduit 110 is not attached to the vacuum port wall 102, a cap (not shown) can be placed over the vacuum port wall 102 to prevent any fluid from leaking from the suction canister 10.

The suction canister 10 is used in the collection of fluids as follows. One end 114 of the suction conduit 110 is affixed to the vacuum port wall 102 as previously described and the other end 118 is placed in communication with the vacuum source 106. One end 86 of the patient conduit 82 is affixed to the patient port wall 78 as previously described and the other end 90 is placed in communication with the fluid to be drained such as in the patient cavity 94. When the vacuum source 106 is on, a vacuum is created in the chamber 18 of the container 14 such that fluid is drawn from the patient cavity 94, through the patient conduit 82 and into the container 14 via the patient port 74.

When the container 14 is filled with fluid or fluid no longer needs to be collected, the patient conduit 82 and the suction conduit 110 can be detached from the lid 70 of the suction canister 10. The caps can then be placed on the patient port wall 78 and the vacuum port wall 114 as previously described to prevent fluid from leaking from the container 14. The suction canister 10 can then be stored until the suction canister is to be drained of its fluid contents.

The apparatus 5 also comprises a drainage device 122 with an upwardly tapered drain conduit 126 and a movable tool 130 as shown in FIG. 1. Preferably, the drainage device 122 uses water pressure and a venturi to create a vacuum that suctions the fluid from the container 14 and delivers this fluid directly to the sanitary sewer line. The drainage device 122 can include a device such as the Deknatel EDUCTOR™ manufactured by Deknatel, Inc. of Fall River, Mass.

To enable the fluid in the container 14 to be drained, the drainage device 122 breaks the protrusion 38 as follows. When a suction canister 10 needs to be drained, the suction canister 10 is placed onto the drainage device 122 so that the drain conduit 126 of the drainage device 122 is inserted into the passageway 42 of the suction canister 10 as shown in FIG. 3. The drain conduit 126 has a configuration that is complementary to the passageway 42. A friction fit between the drain conduit 126 and the first wall portion 54 of the suction canister 10 provides a fluid seal. When the drain conduit 126 is fully wedged into the passageway 42 and the seal formed, the tool 130 is extended upwardly from the drainage device 122 and into the socket 62 of the passageway 42 as shown in FIG. 3. The tool 130 has a configuration that is complementary to that of the socket 62. Referring now to FIG. 5, further upward movement of the tool 130 (as depicted by arrow A) in conjunction with rotational movement of the tool 130 (as depicted by arrow B) breaks the frangible wall portion 66 of the protrusion 38, thereby disconnecting the second wall portion 58 from the first wall portion 54. The breakage of the protrusion 38 allows the fluid within the container 14 to exit the chamber 18 and enter the drainage device 122 via the drain conduit 126. As shown by the small arrows in FIG. 5, the fluid flows through the conduit 126 around the tool 130. The seal between the drain conduit 126 and the first wall portion 54 of the protrusion 38 prevents fluid from flowing anywhere but through the passageway 42 and into the drainage device 122.

During drainage of the fluid from the suction canister 10, the caps on the patient port wall 78 and/or the vacuum port wall 102 can be removed to vent the chamber 18 to aid in drainage of the fluid. Alternatively, a vent could be provided in the drainage device 122 to aid in drainage of the fluid from the suction canister 10.

Various features of the invention are set forth in the following claims.

I claim:

1. A suction canister comprising
   a chamber for collecting body fluids, said chamber being at least partially defined by a wall including a protrusion extending into said chamber and defining passageway having an open outer end and a closed inner end, said protrusion including a frangible wall portion having increased frangibility relative to the remainder of said wall such that said protrusion can be broken to provide communication between said passageway and said chamber,
   a patient port communicating with said chamber for communication with a patient cavity, and
   a vacuum port communicating with said chamber for communication with a vacuum source such that application of a vacuum to said vacuum port creates a vacuum in said chamber and thereby draws body fluids into said chamber via said patient port.

2. A suction canister as set forth in claim 1 wherein said wall includes a first wall portion defining a passageway having an open outer end, and a second wall portion defining a blind inner end of said passageway, and wherein said frangible wall portion connects said first and second wall portions such that said second wall portion can be disconnected from said first wall portion to provide communication between said passageway and said chamber by breaking said frangible portion.

3. A suction canister as set forth in claim 2 and further comprising a container defining said chamber and having an open upper end and a bottom wall, said bottom wall including said wall portions.

4. A suction canister as set forth in claim 3 wherein said container, including said frangible wall portion, is injection molded in a single injection molding process.

5. A suction canister as set forth in claim 3 wherein said passageway is upwardly tapered.

6. A suction canister as set forth in claim 2 and further comprising a lid closing said upper end of said container and having therein said patient port and said vacuum port.

7. A suction canister as set forth in claim 2 wherein said second wall portion defines an outwardly opening, non-circular socket, and wherein said frangible portion is broken by inserting a tool into said socket and rotating said tool.

8. A suction canister as set forth in claim 1 wherein said frangible wall portion is made of plastic.

9. A suction canister as set forth in claim 8 wherein said frangible wall portion is injection molded.

10. A suction canister comprising
   a chamber for collecting body fluids, said chamber being at least partially defined by a wall including a protrusion extending into said chamber and defining a passageway having an open outer end and a closed inner end, said protrusion including a thin portion such that said protrusion can be broken to provide communication between said passageway and said chamber,
   a patient port communicating with said chamber for communication with a patient cavity, and
   a vacuum port communicating with said chamber for communication with a vacuum source such that application of a vacuum to said vacuum port creates a vacuum in said chamber and thereby draws body fluids into said chamber via said patient port.

11. A suction canister as set forth in claim 10 and further comprising a container defining said chamber and having an open upper end and a bottom wall, said bottom wall including said protrusion.

12. A suction canister as set forth in claim 11 wherein said container, including said thin portion, is injection molded in a single injection molding process.

13. A suction canister as set forth in claim 11 wherein said passageway is upwardly tapered.

14. A suction canister as set forth in claim 11 and further comprising a lid closing said upper end of said container and having therein said patient port and said vacuum port.

15. A suction canister as set forth in claim 10 wherein said protrusion defines an outwardly opening, non-circular socket at said inner end of said passageway, and wherein said protrusion is broken by inserting a tool into said socket and rotating said tool.

16. A suction canister as set forth in claim 10 wherein said thin portion is made of plastic.

17. A suction canister as set forth in claim 16 wherein said thin portion is injection molded.

18. Medical apparatus comprising
   a suction canister including a chamber for collecting body fluids, said chamber being at least partially defined by a wall including a protrusion extending into said chamber and defining a passageway having an open outer end and a closed inner end, said protrusion including a thin portion such that said thin portion can be broken to provide communication between said passageway and said chamber, a patient port communicating with said chamber for communication with a patient cavity, and a vacuum port communicating with said chamber for communication with a vacuum source such that application of a vacuum to said vacuum port creates a vacuum in said chamber and thereby draws body fluids into said chamber via said patient port, and
   a drainage device including a mechanism for breaking said thin portion of said protrusion to provide communication between said passageway and said chamber and thereby draining the contents of said chamber.

19. Apparatus as set forth in claim 18 wherein said suction canister wall includes a first wall portion defining said passageway, a second wall portion defining a blind inner end of said passageway, and said thin portion connecting said first and second wall portions, and wherein said drainage device disconnects said second wall portion from said first wall portion to provide communication between said passageway and said chamber by breaking said thin portion.

20. Apparatus as set forth in claim 19 wherein said suction canister includes a container defining said chamber and having an open upper end and a bottom wall, said bottom wall including said wall portions.

21. Apparatus as set forth in claim 20 wherein said passageway is upwardly tapered, and wherein said drainage device includes an upwardly tapered drain conduit adapted to be sealingly wedged into said passageway.

22. Apparatus as set forth in claim 19 wherein said second wall portion defines an outwardly opening, non-circular socket, and wherein said drainage device includes a tool insertable into said socket and rotatable for breaking said thin portion.

23. Apparatus as set forth in claim 18 wherein said wall includes a protrusion extending into said chamber and defining a passageway having an open outer end and a closed inner end, said protrusion including said frangible portion such that said protrusion can be broken to provide communication between said passageway and said chamber.

24. Apparatus as set forth in claim 18 wherein said thin portion is made of plastic.

25. Apparatus as set forth in claim 24 wherein said thin portion is injection molded.

26. Apparatus as set forth in claim 18 wherein said container, including said thin portion, is injection molded in a single injection molding process.

27. A method of removing body fluids from a patient and disposing of the body fluids, said method comprising the steps of
   (a) providing a molded suction canister including a molded-in drain,
   (b) providing a drainage device for automatically opening the molded-in drain and draining the contents of the suction canister,
   (c) collecting body fluids in the suction canister,
   (d) connecting the suction canister to the drainage device, and
   (e) operating the drainage device so that the drainage device opens the drain and drains the contents of the suction canister.

28. A method as set forth in claim 27 wherein step (a) includes the step of providing a suction canister comprising a chamber for collecting body fluids, said chamber being at least partially defined by a wall including the molded-in drain, the drain including a first wall portion defining a passageway having an open outer end, a second wall portion defining a blind inner end of said passageway, and a frangible wall portion connecting said first and second wall portions, and wherein step (e) includes disconnecting said second wall portion from said first wall portion to provide communication between said passageway and said chamber by breaking said frangible portion.

29. A method as set forth in claim 28 wherein step (a) further includes providing a container defining said chamber and having an open upper end and a bottom wall, said bottom wall including said wall portions.

30. A method as set forth in claim 28 wherein step (a) includes said passageway being upwardly tapered, wherein step (b) includes providing said drainage device with an upwardly tapered drain conduit, and wherein step (d) includes inserting the drain conduit into the passageway such that the drain conduit is sealingly wedged into the passageway.

31. A method as set forth in claim 28 wherein step (a) includes said second wall portion defining an outwardly opening, non-circular socket, and wherein step (e) includes breaking said frangible portion by inserting a tool into said socket and rotating said tool.

32. A method as set forth in claim 27 wherein step (a) includes the step of providing a suction canister comprising a chamber for collecting body fluids, said chamber being at least partially defined by a wall including the molded-in drain, the drain including a frangible wail portion, and wherein step (e) includes breaking said frangible wall portion to provide communication with said chamber.

33. A method as set forth in claim 32 wherein step (a) further includes providing a container defining said chamber and having an open upper end and a bottom wall, said bottom wall including said frangible wall portion.

34. A method as set forth in claim 33 wherein step (a) includes said passageway being upwardly tapered, wherein step (b) includes providing said drainage device with an upwardly tapered drain conduit, and wherein step (d) includes inserting the drain conduit into the passageway such that the drain conduit is sealingly wedged into the passageway.

35. Medical apparatus comprising a suction canister including a chamber for collecting body fluids, said chamber being at least partially defined by a wall including a frangible portion such that said frangible portion can be broken to provide communication with said chamber, a patient port communicating with said chamber for communication with a patient cavity, and a vacuum port communicating with said chamber for communication with a vacuum source such that application of a vacuum to said vacuum port creates a vacuum in said chamber and thereby draws body fluids into said chamber via said patient port, and a drainage device including a mechanism for breaking said frangible portion to provide communication with said chamber and thereby draining the contents of said chamber.

36. Apparatus as set forth in claim 35 wherein said suction canister wall includes a first wall portion defining said passageway, a second wall portion defining a blind inner end of said passageway, and said frangible portion connecting said first and second wall portions, and wherein said drainage device disconnects said second wall portion from said first wall portion to provide communication between said passageway and said chamber by breaking said frangible portion.

37. Apparatus as set forth in claim 36 wherein said suction canister includes a container defining said chamber and having an open upper end and a bottom wall, said bottom wall including said wall portions.

38. Apparatus as set forth in claim 37 wherein said passageway is upwardly tapered, and wherein said drainage device includes an upwardly tapered drain conduit adapted to be sealingly wedged into said passageway.

39. Apparatus as set forth in claim 36 wherein said second wall portion defines an outwardly opening, non-circular socket, and wherein said drainage device includes a tool insertable into said socket and rotatable for breaking said frangible portion.

40. Apparatus as set forth in claim 35 wherein said frangible portion is made of plastic.

41. Apparatus as set forth in claim 40 wherein said frangible portion is injection molded.

42. Apparatus as set forth in claim 35 wherein said container, including said frangible portion, is injection molded in a single injection molding process.

* * * * *